US010605900B2

(12) United States Patent
Spuler et al.

(10) Patent No.: US 10,605,900 B2
(45) Date of Patent: Mar. 31, 2020

(54) MICROPULSE DIFFERENTIAL ABSORPTION LIDAR

(71) Applicants: University Corporation for Atmospheric Research, Boulder, CO (US); Montana State University, Bozeman, MT (US); NASA Langley Research Center, Hampton, VA (US)

(72) Inventors: Scott M Spuler, Westminster, CO (US); Kevin S Repasky, Bozeman, MT (US); Amin R Nehrir, Yorktown, VA (US)

(73) Assignees: University Corporation for Atmospheric Research, Boulder, CO (US); Montana State University, Bozeman, MT (US); NASA Langley Research Center, Hampton, VA (US)

( * ) Notice: Subject to any disclaimer, the term of this patent is extended or adjusted under 35 U.S.C. 154(b) by 534 days.

(21) Appl. No.: 15/139,925

(22) Filed: Apr. 27, 2016

(65) Prior Publication Data

US 2017/0212219 A1 Jul. 27, 2017

Related U.S. Application Data

(60) Provisional application No. 62/167,118, filed on May 27, 2015.

(51) Int. Cl.
| | | |
|---|---|---|
| *G01S 7/48* | (2006.01) | |
| *G01S 7/481* | (2006.01) | |
| *G01S 7/484* | (2006.01) | |
| *G01S 17/10* | (2020.01) | |
| *G01S 17/95* | (2006.01) | |

(Continued)

(52) U.S. Cl.
CPC ......... *G01S 7/4814* (2013.01); *G01N 21/538* (2013.01); *G01S 7/484* (2013.01); *G01S 7/4812* (2013.01); *G01S 7/4816* (2013.01); *G01S 17/107* (2013.01); *G01S 17/95* (2013.01); *G01N 2021/1795* (2013.01); *G01N 2021/4709* (2013.01); *Y02A 90/19* (2018.01)

(58) Field of Classification Search
None
See application file for complete search history.

(56) References Cited

U.S. PATENT DOCUMENTS

| 5,220,164 A * | 6/1993 | Lieber ................... G01S 7/4813 250/214 VT |
|---|---|---|
| 2007/0024849 A1* | 2/2007 | Carrig ................... G01N 21/21 356/337 |

(Continued)

*Primary Examiner* — Luke D Ratcliffe
(74) *Attorney, Agent, or Firm* — The Ollila Law Group LLC

(57) ABSTRACT

A shared optics and telescope, a filter, and a micropulse differential absorption LIDAR are provided, with methods to use the same. The shared optics and telescope includes a pair of axicon lenses, a secondary mirror, a primary mirror including an inner mirror portion and an outer mirror portion, the inner mirror portion operable to expand the deflected annular transmission beam, and the outer mirror portion operable to collect the return signal. The filter includes an etalon and a first filter. The micropulse differential absorption LIDAR includes first and second laser signals, a laser transmission beam selection switch, a first laser return signal switch, and a toggle timer.

18 Claims, 5 Drawing Sheets

(51) Int. Cl.
*G01N 21/53* (2006.01)
*G01N 21/17* (2006.01)
*G01N 21/47* (2006.01)

(56) References Cited

U.S. PATENT DOCUMENTS

2015/0109603 A1* 4/2015 Kim .................. G01S 17/10
  356/4.07
2016/0223653 A1* 8/2016 Hutson .................. G01S 17/08

* cited by examiner

MICROPULSE DIFFERENTIAL ABSORPTION LIDAR

CROSS REFERENCE TO RELATED APPLICATIONS

This patent application claims the benefit of and priority to U.S. Provisional Patent Application No. 62/167,118, filed on May 27, 2015, the contents of which are hereby incorporated by reference in their entirety.

STATEMENT REGARDING FEDERALLY SPONSORED RESEARCH OR DEVELOPMENT

The invention described herein was made in part by an employee of the United States Government and may be manufactured and used by or for the Government of the United States of America for governmental purposes without the payment of any royalties thereon or therefore. The U.S. Government also has the right in limited circumstances to require the patent owner to license others on reasonable terms as provided for by the terms of Agreement No. AGS-0753581, awarded by a National Science Foundation and National Center for Atmospheric Research cooperative agreement, and Agreement No. 1206166, awarded by the National Science Foundation.

TECHNICAL FIELD

The present Application is directed towards LIDAR systems, and more particularly, to a micropulse differential absorption LIDAR system.

BACKGROUND OF THE INVENTION

The planetary boundary layer (PBL), the lowest part of the troposphere, contains the majority of the atmospheric water vapor. The rapidly changing spatial and temporal distribution of water vapor contained within this part of the atmosphere influences convective processes that drive weather and circulation patterns and affects radiative transfer, the water cycle, and soil moisture. The ability to continuously measure water vapor distributions within the lower troposphere has been identified as a high priority measurement capability needed by both the weather forecasting and climate science communities. Atmospheric studies have listed high-resolution vertical profiles of humidity in the lower troposphere and PBL height as high priority observations that need to be addressed for the next generation mesoscale weather observation network. In addition, these observations are of high importance to the National Weather Service and other Federal agencies for evaluation of forecast impact in severe weather plus quantitative precipitation forecasts. Yet, accurate, high-resolution, continuous measurements of water vapor remain a key observational gap for the mesoscale weather and climate process studies communities.

Local soundings of high vertical resolution atmospheric state parameters via radiosonde measurements combined with global coverage of low vertical resolution state parameters via satellite-based measurements form the backbone of observations used for weather forecasting. But the limited spatial and temporal resolution of the current state of technology prohibits observations of key atmospheric features required for accurate forecasting of mesoscale high-impact weather events like thunderstorms. Passive remote sensors such as infrared and microwave radiometers are useful at low ranges close to the surface but in general provide low vertical resolutions. The atmospheric emitted radiance interferometer (AERI) is a passive remote sensing instrument that utilizes an interference technique to retrieve atmospheric emitted radiance. Starting with an initial temperature and water vapor profiles based on statistical models, an iterative solution to the radiative transfer equations is utilized to reproduce the measured atmospheric emitted radiance. This iterative solution provides the final temperature and water vapor profiles for clear sky conditions up to approximately 3 km with a 250 m range resolution. During cloudy conditions, retrieval of temperature and water vapor profiles are sensitive to the cloud properties leading to larger errors in the retrieved temperature and water vapor profiles. During cloudy conditions a separate measurement of the cloud base height is often required.

Raman LIDAR is an active remote sensing technique that is capable of monitoring water vapor throughout the troposphere. The Raman LIDAR technique utilizes a high power pulsed laser transmitter to actively illuminate the atmosphere. Range information is determined by the time of flight of the laser pulse traveling from the beam transmitter to the scatterer (aerosols, clouds, and molecules) and back to the receiver. The frequency shift due to the inelastic Raman scattering allows the scattering molecule to be identified while the intensity of the scattered signal can be used to determine the water vapor mixing ratio. Raman LIDAR typically require a high pulse energy and large receiver aperture due to the small scattering cross section associated with inelastic Raman scattering. Furthermore, Raman LIDAR typically require a calibration technique based on an ancillary measurement for quantitative water vapor retrievals.

Differential absorption LIDAR (DIAL) is another active remote sensing technique used to directly measure column and range resolved profiles of atmospheric trace gases. A laser source emits a pulse of light (typically a few nanoseconds to 1 microsecond in duration), and as the pulse propagates, the photons interact with particles in the atmosphere. Some of these interactions, such as Mie and Rayleigh scattering, result in backscattered photons. The photons are collected by a detector and recorded as function of time. This time-of-flight data has a direct correspondence with the range (distance) at which the scattering event occurred. DIAL utilizes a laser transmitter capable of operating at two closely spaced wavelengths, one wavelength which is located at or near the absorption feature for the molecule of interest, referred to as the online wavelength and the other located away from the same absorption feature, referred to as the offline wavelength. If the online and offline wavelengths are closely spaced, then the only difference between the return signals results from molecular absorption. Using an a priori knowledge of the differential absorption cross section of the molecule of interest available, for example, in the HIgh-resolution TRANsmission molecular absorption database (HITRAN), the ratio of the online and offline return signals over a selected range within the atmosphere can be used to determine a molecular number density. The DIAL technique provides the advantages of not requiring a calibration or ancillary measurements, and providing a direct measurement of the water vapor number density. However, the DIAL technique requires a pulsed laser with high spectral fidelity and agility capable of operating at two separate wavelengths.

Co-axial or concentric geometry LIDARs are used in the LIDAR community as a way to propagate the transmitted beam into the receiver field of view. However, these systems often use a separate mirror concentric with the telescope secondary mirror for laser transmission. Greater stability and a larger beam expansion, required for eye safety in compliance with Federal Aviation Administration regulations, can be achieved with a shared telescope design approach which utilizes the receiver telescope to expand and transmit the outgoing laser beam. Prior shared telescope designs have illuminated the entire primary mirror to expand the beam with the telescope, however, losing light blocked by the secondary mirror. For a micropulse LIDAR system using a low-power laser transmitter, inefficiently transmitting the beam through the telescope impacts performance. Higher efficiency designs have been achieved by shaping the transmit beam into an annulus with an axicon lens pair. Beam shaping alone cannot solve the performance problems experienced by prior micropulse LIDAR systems if the beam is expanded to the full diameter of the telescope, however, because prior designs have needed polarization transmit/receive switches to separate transmit and receive paths in the shared telescope. The polarization transmit/receive switches have provided for poor isolation between transmit and receive paths.

Removing solar background light during the daytime and when there are cloudy conditions from the return signal of a LIDAR is also important. Prior instruments used a narrowband filter having a 250 pm full width half maximum (FWHM) bandpass, permitting measurements up to 3 km in altitude to be obtained. Greater altitudes, and therefore better background light filtering are needed, however.

Prior DIAL designs have used a fiber coupled MEMS switch to alternate between the online and offline wavelength which, exhibiting approximately 1 ms 10/90 switching time. The data acquisition system utilized a single channel of a four channel multi-channel scalar photon counting card which had 2 buffers to allow for continuous read and write operations to occur. To avoid mixing the signals within the data acquisition system, a first laser frequency was transmitted for 3 seconds, followed a 3 second dead time when the wavelength switch was changed, then a second laser frequency was transmitted for 3 seconds. Switching with the MEMS switch created several performance limitations. First, the dead time resulted in a 60% duty cycle (i.e., the reported water vapor integration time of 20 minutes was equivalent to a 33 minutes temporal resolution). Second, wavelength switching on timescales of several seconds can result in errors due to rapid changes between the online and offline backscattered signals resulting from fluctuations in the aerosol distributions on short time scales. A higher duty cycle DIAL instrument would allow the acquisition of more robust data collection.

What is needed is a micropulse differential absorption LIDAR instrument that is capable of autonomous long term field operation under an expanded set of atmospheric conditions, such as during the daytime, with cloud cover, and during times of rapidly changing atmospheric conditions. Ideally, the micropulse differential absorption LIDAR device will be eye-safe, will be mechanically and thermally stable for the beam transmitter and receiver, will have an improved duty cycle, will provide excellent isolation between the transmitted and received signals, and will offer improved performance.

SUMMARY OF THE INVENTION

A shared optics and telescope for transmitting a transmission beam and receiving a return signal is provided. The shared optics and telescope includes a pair of axicon lenses operable to shape the transmission beam into an annular beam having an outer diameter and an inner diameter. The shared optics and telescope further includes a secondary mirror operable to deflect the annular beam into a deflected annular transmission beam. The shared optics and telescope further includes a primary mirror that includes an inner mirror portion and an outer mirror portion, the inner mirror portion being operable to expand the deflected annular transmission beam, and the outer mirror portion being operable to collect the return signal.

A method for transmitting a transmission beam and receiving a return signal through a shared optics and telescope is provided. The method comprises the step of shaping the transmission beam into an annular pattern using a pair of axicon lenses to create an annular transmission beam. The method further comprises the step of deflecting the transmission beam towards a primary mirror using a secondary mirror to generate a deflected annular transmission beam. The method further comprises the step of expanding the deflected annular transmission beam using an inner mirror portion of the primary mirror. The method further comprises the step of collecting a return signal using an outer mirror portion of the primary mirror.

A filter for a micropulse differential absorption LIDAR is provided. The filter includes an etalon including a free spectral range substantially the same as a difference between a first laser wavelength and a second laser wavelength. The etalon further includes a finesse providing substantial background noise suppression and substantially constant transmission of the first laser wavelength and the second laser wavelength over a predetermined range of wavelengths. The filter further includes a first filter having a first filter bandpass selected to include the first wavelength and the second wavelength.

A method for filtering a return signal from a micropulse differential absorption LIDAR is provided. The method comprises the step of filtering the return signal using an etalon. The etalon includes a free spectral range that is substantially the same as a difference between a first laser wavelength and a second laser wavelength. The etalon further includes a finesse providing substantial background noise suppression and substantially constant transmission of the first laser wavelength and the second laser wavelength over a predetermined range of wavelengths. The method further comprises the step of filtering the return signal received from the etalon using a first filter, the first filter having a first filter bandpass selected to include the first wavelength and the second wavelength.

A micropulse differential absorption LIDAR is provided, including a first laser signal, and a second laser signal. The LIDAR further includes a laser transmission beam selection switch operable to toggle between including the first laser signal or the second laser signal in a transmission beam. The LIDAR further includes a first laser return signal switch operable to toggle between a first counter when the return signal includes a backscattered light from the first laser signal and a second counter when the return signal includes a backscattered light from the second laser signal. The LIDAR further includes a toggle timer operable to substantially concurrently toggle the laser transmission beam selection switch and the first laser return signal switch.

A method for operating a micropulse differential absorption LIDAR is provided. The method comprises the step of receiving a first laser signal. The method further comprises the step of receiving a second laser signal. The method further comprises the step of toggling between including the first laser signal and the second laser signal in a transmission beam using a laser transmission beam selection switch. The method further comprises the step of toggling between a first counter when the return signal includes a backscattered light from the first laser signal and a second counter when the return signal includes a backscattered light from the second laser signal using a first laser return signal switch. The method further comprises the step of toggling the laser transmission beam selection switch and the first laser return signal switch substantially concurrently using a toggle timer.

DETAILED DESCRIPTION OF THE INVENTION

FIGS. 1-5 and the following description depict specific examples to teach those skilled in the art how to make and use the best mode of the Application. For the purpose of teaching inventive principles, some conventional aspects have been simplified or omitted. Those skilled in the art will appreciate variations from these examples that fall within the scope of the Application. Those skilled in the art will appreciate that the features described below can be combined in various ways to form multiple variations of the Application. As a result, the Application is not limited to the specific examples described below, but only by the claims and their equivalents.

Figure 1:
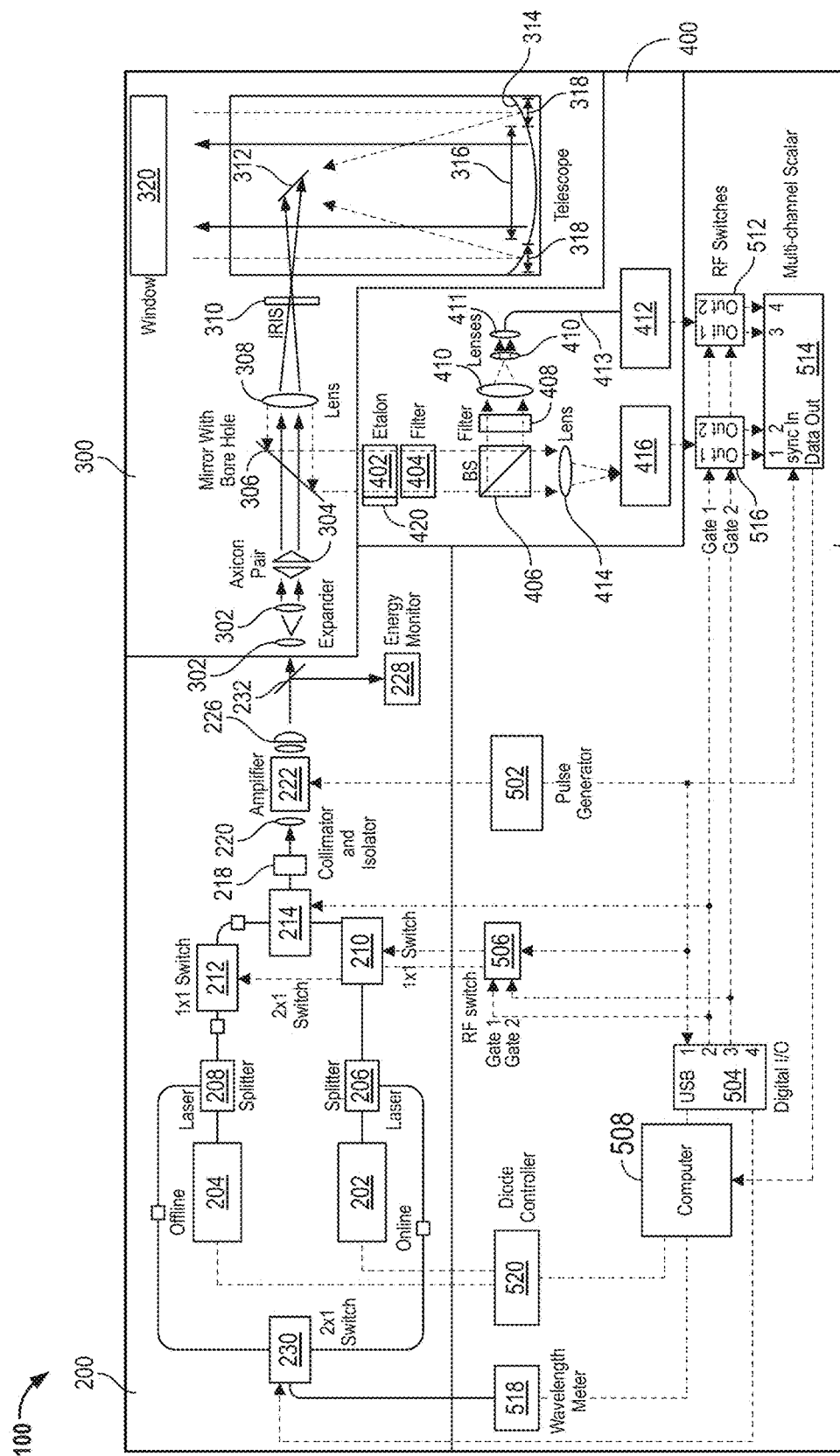
FIG. 1 depicts micropulse differential absorption LIDAR 100, in accordance with an embodiment.

FIG. 1 depicts micropulse differential absorption LIDAR 100. Micropulse differential absorption LIDAR 100 includes a beam transmitter 200, a shared optics and telescope 300, an optical receiver 400, and an electronics 500. Micropulse differential absorption LIDAR 100 is a LIDAR that can operate with two separate lasers. For example, micropulse differential absorption LIDAR 100 may be a differential absorption LIDAR used to detect water vapor, or another molecular species.

Beam Transmitter

Micropulse differential absorption LIDAR 100 includes beam transmitter 200. Beam transmitter 200 includes a first laser 202, an second laser 204, splitters 206, and 208, first switch 210, second switch 212, a laser transmission beam selection switch 214, a first collimator and isolator 218, a coupler 220, an amplifier 222, a circular collimator 226, an energy monitor 228, a 2 to 1 switch 230, and a window 232.

In embodiments, micropulse differential absorption LIDAR 100 may be a differential absorption LIDAR. Those skilled in the art will readily understand that differential absorption and water vapor measurements are one possible micropulse differential absorption LIDAR application, and other micropulse differential absorption LIDAR applications are possible.

First laser 202 and second laser 204 are each operable to generate a transmission beam. In embodiments, first laser 202 may produce an online frequency selected to produce an on-resonance absorption response, and second laser 204 may produce an offline frequency selected to produce an off-resonance absorption response for a molecular species of interest. For example, first laser 202 and second laser 204 may operate in continuous wave mode, producing up to 80 mW of power with a measured line width less than 1 MHz. In embodiments, first laser 202 and second laser 204 may each be a distributed Bragg reflector laser diode. When combined with an amplifier, first laser 202 and second laser 204 may be alternatively used to produce a transmission beam operable to make differential absorption LIDAR measurements.

The output from first laser 202 is transmitted into splitter 206, and the output of second laser 204 is transmitted into splitter 208. Splitter 206 is operable to divide the transmission beam output from first laser 202 between switch 230 and first switch 210. Splitter 208 is operable to divide the transmission beam output from second laser 204 between switch 230 and second switch 212. Switch 230 is operable to enable monitoring of the stability of first laser 202 or second laser 204 via a wavelength reference 518. For example, wavelength reference 518 may be a wavelength meter.

First switch 210 and second switch 212 may be 1×1 switches that are toggled off and on to modulate the respective first laser 202 and second laser 204 pulse signals, respectively. In embodiments, amplifier 222 may commanded on substantially concurrently with the transmission of a laser pulse, as described below.

The transmission beam next passes from first switch 210 and second switch 212 onto laser transmission beam selection switch 214. Laser transmission beam selection switch 214 is electronically controllable to transmit the transmission beam from either first switch 210, online laser 202, or second switch 212, offline laser 204. In embodiments, laser transmission beam selection switch 214 may be used to alternate the first laser 202 and second laser 204 seed pulse signals to amplifier 222 at high repetition rates. In embodiments, beam transmitter 200 may be operated with the online and offline wavelengths interleaved at rates up to 9 kHz. In embodiments, switches 210, 212, 214, and 230 may be fast electro-optic switches with 200 ns switching speed driver boards.

Advantageously, the two-stage optical switch arrangement provided by switches 210, 212, and 214 may provide ~40 dB isolation between the online and offline signals (each switch has ~20 dB crosstalk) to maintain a high spectral purity in the transmitted pulses. The two-stage switch arrangement may further help increase the duty cycle at which micropulse differential absorption LIDAR 100 is operated, as will be further discussed below with respect to electronics 500.

After the transmission beam emerges from laser transmission beam selection switch 214, the transmission beam passes into first collimator 218. In embodiments, first collimator 218 may include an aspheric collimation lens. In further embodiments, collimator 218 may further include an isolator. Collimator 218 is operable to prevent unwanted feedback from affecting the power output and spectral stability of the transmission beam. In embodiments, collimator and isolator 218 may further include a half wave plate that is used to set the polarization of the light to that of what amplifier 222 requires.

After the transmission beam emerges from collimator 218, it enters coupler 220. In embodiments, coupler 220 may be an aspheric lens used to couple light into amplifier 222. Advantageously, this may prevent unwanted feedback from amplifier 222 reach to first laser 202 and second laser 204.

The collimated and isolated transmission beam next passes through amplifier 222. First laser 202 and second laser 204 act a seed laser to amplifier 222. In embodiments, amplifier 222 may be a tapered semiconductor optical amplifier (TSOA). For example, amplifier 222 may be a 4 mm long TSOA used to amplify and pulse the beam transmitter.

Amplifier 222 may be driven with a pulse generator 502. For example, pulse generator 502 may be a commercial pulse generator such as the PCX-7420 model manufactured by Directed Energy, Inc, having a programmable pulse duration, pulse repetition rate, and peak pulse current. Standard settings for the PCX-7420 model pulse generator include a pulse current of 10 A with a 1.1 µs pulse duration and a 9 kHz pulse repetition frequency. In embodiments, pulse generator 502 may be used as a master clock for micropulse differential absorption LIDAR 100. For example, the leading edge of pulse generator 502 may also be used to trigger first switch 210, second switch 212, and laser transmission beam selection switch 214, directly and via an I/O digital counter in a digital IO board 404, as will be further described below. Therefore, although a 1.1 µs current pulse may be applied to amplifier 222, the resulting amplified transmission beam laser pulse may have a 900 ns duration due to the 200 ns rise time of the 1×1 switch driver. The resulting amplified transmission beam laser pulse may have a transmitted pulse energy of 50 µJ to 100 µJ at an amplifier current of 5-10 A.

In the example implementation of amplifier 222 being a TSOA, the astigmatic geometry of the output facet of the TSOA may further include shaping the transmission beam with a beam shaping pair of lenses 226 to achieve a nominally circular collimated beam. For example, the beam shaping pair of lenses 226 may include a spherical lens and a cylindrical lens.

Following the beam shaping pair of lenses 226, window 232 is used to direct approximately 4% of the transmission beam to energy monitor 228, or a photodetector. Energy monitor 228 is operable to monitor the average output power from beam transmitter 200.

Shared Optics and Telescope

Micropulse differential absorption LIDAR 100 further includes shared optics and telescope 300. Shared optics and telescope 300 includes a beam expander 302, axicon lenses 304, a mirror with bore hole 306, a telescope lens 308, an iris 310, a primary mirror 312, a secondary mirror 314, an inner mirror portion 316, an outer mirror portion 318, and window 320.

Shared optics and telescope 300 is operable to transmit the transmission beam received from beam transmitter 200. Shared optics and telescope 300 is also operable to receive a return signal and to transmit the return signal onward to electronics 400. Shared optics and telescope 300 may be a Newtonian telescope f/3 design.

The transmission beam first enters beam expander 302. Beam expander 302 is operable to expand the collimated signal received from beam shaping pair of lenses 226. In embodiments, beam expander 302 expands the cross sectional area of the transmission beam 2 times.

The transmission beam is next incident on axicon lenses 304. Axicon lenses 304 are a matched pair of axicon, or conical lenses that shape the transmission beam into a annular transmission beam. The annular beam shaped by axicon lenses 304 includes an outside diameter and an inside diameter. In embodiments, the outside beam diameter of the annular transmission beam may be determined by the axicon spacing and wedge angle while the inside beam diameter may be determined by the incident beam diameter. Advantageously, beam expander 302 and axicon lenses 304 shape the annular transmission beam efficiently for transmission through the telescope.

After the transmission beam emerges from axicon lenses 304 as an annular transmission beam, it next passes through the center bore of a mirror with bore hole 306. In embodiments, the mirror with bore hole 306 may include a 10 mm bore hole in its center to allow the annular transmission beam to pass.

The collimated, annular transmission beam is next incident on telescope lens 308 which focuses the annular transmission beam. In embodiments, telescope lens 308 may have a 60 mm focal length. In embodiments, the f-number (ratio of focal length to diameter) of the telescope lens 308 may be selected to match the f-number of the shared telescope. Advantageously, matching the f-number of the telescope lens 308 and shared optics and telescope 300 reduces vignetting and helps collimate the outgoing focused annular transmission beam as it exits the telescope.

The transmitted beam next passes through iris 310 and onto secondary mirror 312. Secondary mirror 312 deflects the focused annular transmission beam towards primary mirror 314 to generate a deflected annular transmission beam.

Primary mirror 314 includes circular inner mirror portion 316 and annular outer mirror portion 318. Circular inner mirror portion 316 receives and then expands the deflected annular transmission beam. In an example embodiment, primary mirror 314 has a diameter of 406-mm and an f-number of 3. The deflected annular transmission beam is expanded by telescope lens 308 and collimated with the inner mirror portion 316 of the primary mirror 314, generating a transmitted beam with an outer beam diameter of approximately 180 mm and an inner beam diameter of approximately 70 mm. Advantageously, the width of the inner beam diameter may allow the annular-shaped transmission beam to clear the secondary mirror as it exits the telescope, minimizing losses in the transmitter beam pulse energy.

Shared optics and telescope 300 may further include window 320. Window 320 may be operable to allow the transmission beam and return signal to pass, while shielding shared optics and telescope 300 from contaminants.

Advantageously, shared optics and telescope 300 shapes a transmission beam that is a factor 20× more opto-mechanically stable than prior co-axial telescope designs, because the transmission beam is expanded by the telescope after the transmit mirror.

The transmitted beam described with regards to shared optics and telescope 300 may be eye safe at the exit of window 320 as defined by the American National Standards Institute (ANSI) standard Z136.1-2014. The ANSI regulation sets the single-pulse maximum permissible exposure (MPE) for a 1 s duration pulse at the 830 nm wavelength at 360 $nJ/cm^2$. A repetitively pulsed LIDAR system must therefore feature less than both the multiple energy and multiple power MPEs—which for the example beam transmitter 200 and shared optics and telescope 300 system, operating at the 9 kHz repetition rate, is 203 nJ/cm² and 1.83 mW/cm², respectively. Because the transmission beam is expanded 2× at expander 302 and 20× at the inner mirror portion 316 of primary mirror 314, the 1.83 mW/cm² MPE limit is not exceeded, as verified with a prototype beam transmitter 200 and shared optics and telescope 300 in a laboratory.

A return signal including light scattered in the atmosphere is collected by the shared optics and telescope 300. Outer mirror portion 318 of primary mirror 314 collects the scattered return signal. In an example embodiment, outer mirror portion 318 may be an annulus with an inner diameter of 406 mm, an outer diameter of 528 mm.

After being deflected at secondary mirror 312 and passing through iris 310, return signal is collimated by telescope lens 308. The return signal is then incident on and deflected by the mirror portion of mirror with bore hole 306. Mirror with bore hole 306 only collects light from a diameter that is greater than 200 mm when received at primary mirror 314, which provides excellent signal isolation from the transmitted beam.

Optical Receiver

Micropulse differential absorption LIDAR 100 includes optical receiver 400. Optical receiver 400 includes an etalon 402, a filter 404, a beam splitter 406, a filter 408, reducing lenses 410, far-field focusing lens 411, a far-field photon counter 412, a near-field focusing lens 414, and a near-field photon counter 416.

Optical receiver 400 is operable to receive the return signal from shared optics and telescope 300 and to isolate the relevant first and second laser wavelengths so that the return signal can be measured. In embodiments, optical receiver 400 may also be operable to isolate return signal from the far-field and the near-field.

Figure 2A:
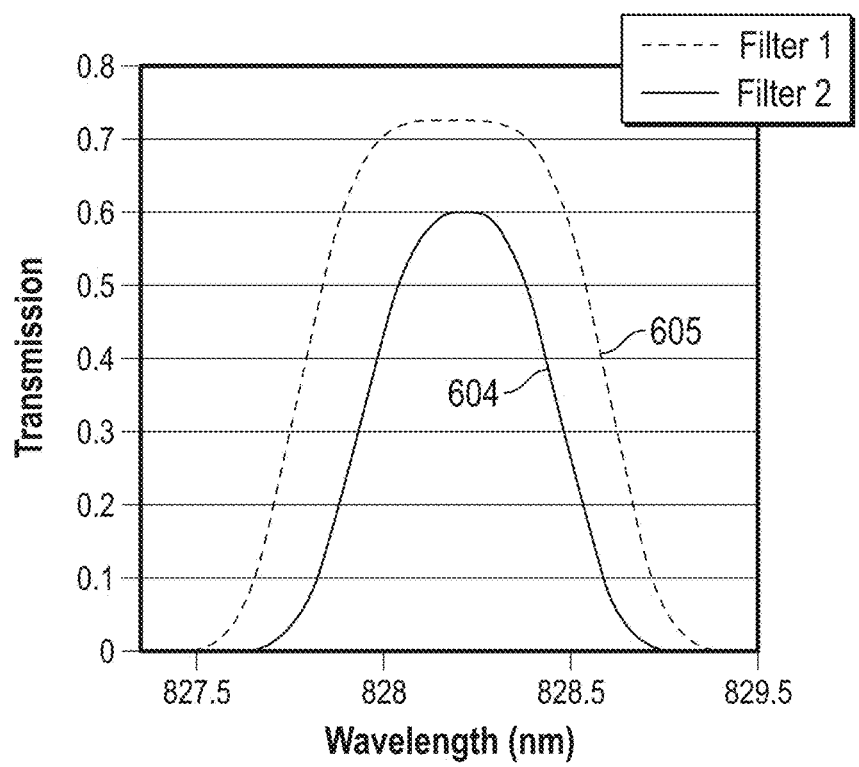
FIG. 2A depicts passband plot of an interference filter, in accordance with an embodiment.
Figure 2B:
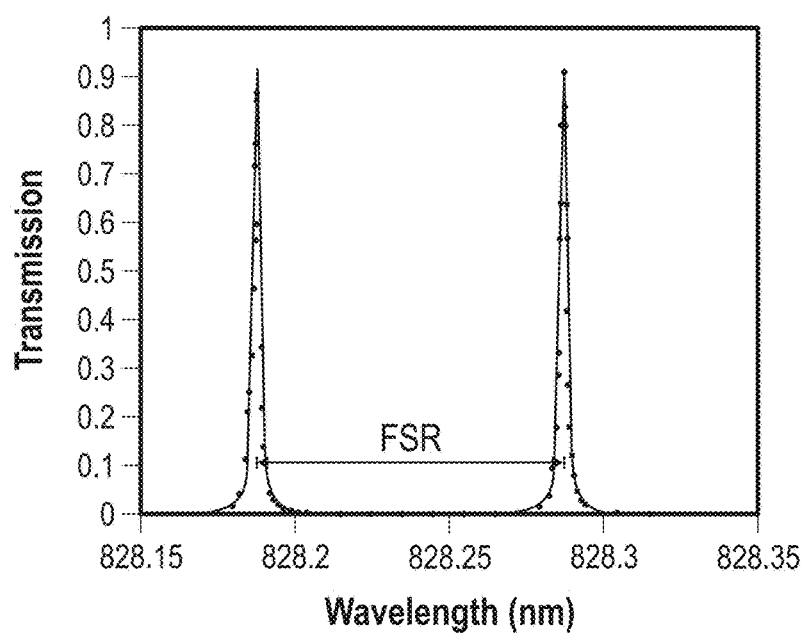
FIG. 2B depicts an example of an etalon transmission measurement made with a differential absorption LIDAR 100, in accordance with an embodiment.

After being deflected by mirror with bore hole 306 upon exiting telescope 300, the return signal next passes through etalon 402 and then filter 404 of optical receiver 400. Etalon 402 is a Fabry-Perot interferometer, operable to isolate or filter the two wavelengths of light representing adjacent interferometer cavity modes from the return signal. FIG. 2B provides an example transmission curve for etalon 402 as a function of wavelength. It may be seen in FIG. 2B that example etalon 402 allows two narrow spectral lines to pass. FIG. 2B depicts an example etalon transmission measurement made with a prototype micropulse differential absorption LIDAR 100, overlaid with a fit to the data based on a Equation 1 below:

$$T_{etalon} = \frac{(1-R)^2}{1+R^2-2R\cos\theta}. \quad \text{(Equation 1)}$$

In Equation 1, $T_{etalon}$ is the etalon transmission, R is the etalon mirror reflectivity, and θ is the round trip phase accumulation, which may be further represented by Equation 2 below:

$$\theta = 4\pi\frac{nL}{\lambda}. \quad \text{(Equation 2)}$$

In Equation 2, L is the length of the cavity, n is the index of refraction of the media within the cavity, and λ is the wavelength of light in the cavity.

The free spectral range (FSR) of etalon 402, the distance between the cavity modes, or the adjacent or optical cavity spacing, is the difference between the two wavelengths that may be transmitted through etalon 402. FIG. 2B depicts an example FSR. FSR may be determined by Equation 3 below:

$$FSR = \frac{c}{2nL}. \quad \text{(Equation 3)}$$

In embodiments, etalon 402 may be designed so that FSR is substantially the same as a difference between the first and second wavelengths of the micropulse differential absorption LIDAR. For example, etalon 402 may be designed to provide an FSR that is substantially equivalent to the difference between an online and an offline wavelength for differential absorption LIDAR applications. Advantageously, selecting the FSR to be substantially the same as the distance between the online and offline wavelengths may allow etalon 402 to be operated without tuning during operation, allowing for simple temperature control. Because both the online and offline wavelengths may be resonant and no tuning is required, etalon 402 may support the rapid switching between the online and offline wavelengths.

The spectral location of the cavity modes may be adjusted by controlling the temperature of etalon 402 in a way that maintains the fixed FSR spacing between the cavity modes. In embodiments, etalon 402 may therefore be housed in or coupled to a temperature controller 420. An etalon mount may be designed to easily integrate with a tube assembly housing optics for optical receiver 400. In an embodiment, the operating temperature of etalon 402 may be controlled via a thermoelectric cooler (TEC) using a temperature controller with a temperature stability of 0.01 C. The temperature controller 420 may therefore enable the operating temperature of etalon 402 to be adjusted to be resonant with the first laser 202 and second laser 204 wavelengths.

Figure 3A:
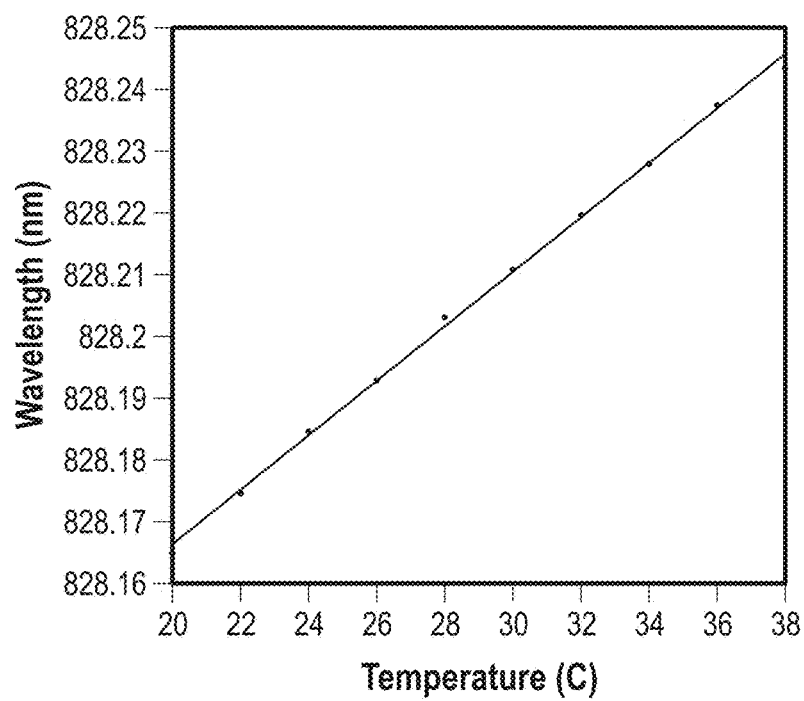
FIG. 3A depicts a plot of a resonant wavelength as a function of temperature for an etalon, in accordance with an embodiment.

For example, FIG. 3A depicts a plot of the resonant wavelength as a function of temperature for a prototype of etalon 402. The circles depicted in FIG. 3A represent measured resonant wavelength values, while the solid line represents a linear fit showing a temperature tuning rate of $d\lambda/dT=0.00441$ nm/C$^{-1}$. From FIG. 3A, it may be seen that a change in temperature of 22.4 C is needed to tune etalon 402 through a full free spectral range.

The sharpness, or the full width half max of the cavity mode wavelengths, is further determined by the finesse $\mathcal{F}$ of etalon 402. The finesse $\mathcal{F}$ is related to the mirror reflectivity by Equation 4:

$$\mathcal{F} = \frac{\pi\sqrt{R}}{1-R}, \quad \text{(Equation 4)}$$

where R is the etalon mirror reflectivity. By selecting an etalon mirror reflectivity, it may therefore be possible to select a finesse value that is large enough to provide substantial background noise suppression.

The locking stability of first laser 202 and second laser 204 and the temperature stability of etalon 402 may further affect the transmission properties of etalon 402. The effects of locking stability on the cavity transmission can be modeled using Equation 1, with the round trip phase accumulation θ as determined by Equation 5:

$$\theta = \pi \frac{\Delta\lambda}{FSR_\lambda}. \quad \text{(Equation 5)}$$

In Equation 5, $\Delta\lambda$ is the detuning from the resonant peak in wavelength and $FSR_\lambda$ is the free spectral range in wavelength. The temperature stability of etalon 402 may therefore be modeled using the measured temperature tuning rate, $d\lambda/dT=0.00441$ nm/C discussed with reference to FIG. 3A and a stability temperature for the etalon of T=0.01 C.

Figure 3B:
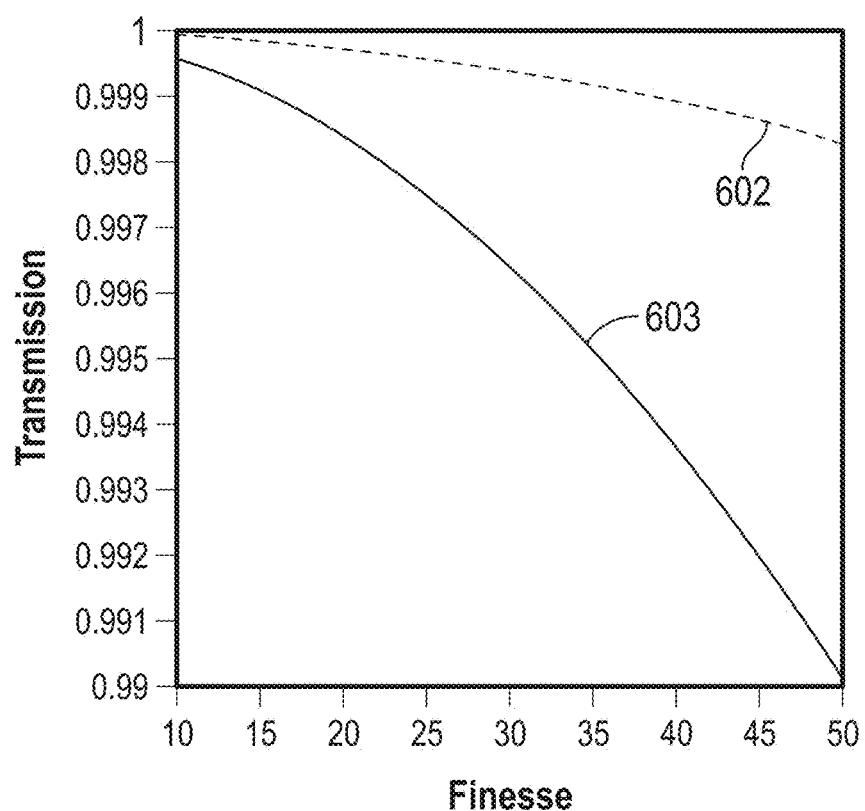
FIG. 3B depicts a plot of a measured prototype etalon cavity transmission as a function of finesse, in accordance with an embodiment.

FIG. 3B depicts a plot of the measured prototype etalon 402 cavity transmission as a function of finesse. FIG. 3B depicts etalon cavity transmission as a function of finesse for a locking stability of 0.0002 nm, plot 602. FIG. 3B further depicts a temperature stability of 0.01 C, plot 603.

In embodiments, the finesse of the etalon may therefore further provide for substantially constant transmission of the first laser wavelength and the second laser wavelength over a predetermined range of wavelengths. The predetermined range of wavelengths may include, for example, the locking stability of the first laser wavelength and the second laser wavelength. The predetermined range of wavelengths may further include changes due to temperature stability region of the etalon. In embodiments, the temperature stability of the etalon may be determined in part by a temperature controller coupled to the etalon, such as temperature controller 420.

In embodiments, etalon 402 may therefore include a finesse providing substantial background noise suppression and substantially constant transmission of the first laser wavelength and the second laser wavelength over the predetermined range of wavelengths. For example, a finesse of 40-50 may be large enough to reduce background noise, and small enough to maintain a substantially constant transmission of the predetermined range of wavelengths. Advantageously, the finesse of etalon 402 may therefore be selected to suppress background noise and maintain a substantially constant transmission, regardless of laser and etalon fluxuations.

After exiting etalon 402, return signal enters first filter 404. First filter 404 may include a filter bandpass selected to include the online wavelength and the offline wavelength. For example, the filter bandpass may be selected such that the transmission between the first laser wavelength and the second laser wavelength are maximized. The filter bandpass may be further selected so that the transmission outside a wavelength range between the first laser wavelength and the second laser wavelength exponentially drops to zero.

In embodiments, first filter 404 may be an interference filter having a double cavity design. For example, FIG. 2A depicts passband plot 605. Passband plot 605 represents a fit to a measured filter transmission for a full width half maximum passband of 500 pm. In an embodiment filter 404 may use a double cavity design to provide a first filter passband having a substantially constant transmission rate between the first and second wavelengths, as depicted by bandpass 605.

Upon exiting filter 404, return signal enters beamsplitter 406. Beamsplitter 406 is operable to split the return signal along two pathways, a near-field return signal path and a far-field return signal path. The near-field channel includes near-field focusing lens 414 and near-field photon counter 416. The far-field channel includes far-field filter 408, reducing lenses 410, and far-field focusing lens 411. In embodiments, beamsplitter 406 may transmit 10% of return signal to the near-field channel and reflect 90% of return signal to the far-field channel. This is not intended to be limiting, however. Other distributions of light are also possible for the near-field and far-field channel, as will be understood by those of skill in the art.

The near-field channel includes near-field focusing lens 414. Near-field focusing lens 414 is operable to focus light onto near-field photon counter 416. In embodiments, near-field focusing lens 414 may be a 20 mm focal length lens operable to focus return signal on near-field photon counter 416. In embodiments, near-field photon counter 416 may be a free-space avalanche photodiode (APD). The active area of the APD may act as a field stop resulting in a 451 µrad wide field-of-view (FOY) capturing a view corresponding to the near-field return signal.

Figure 2C:
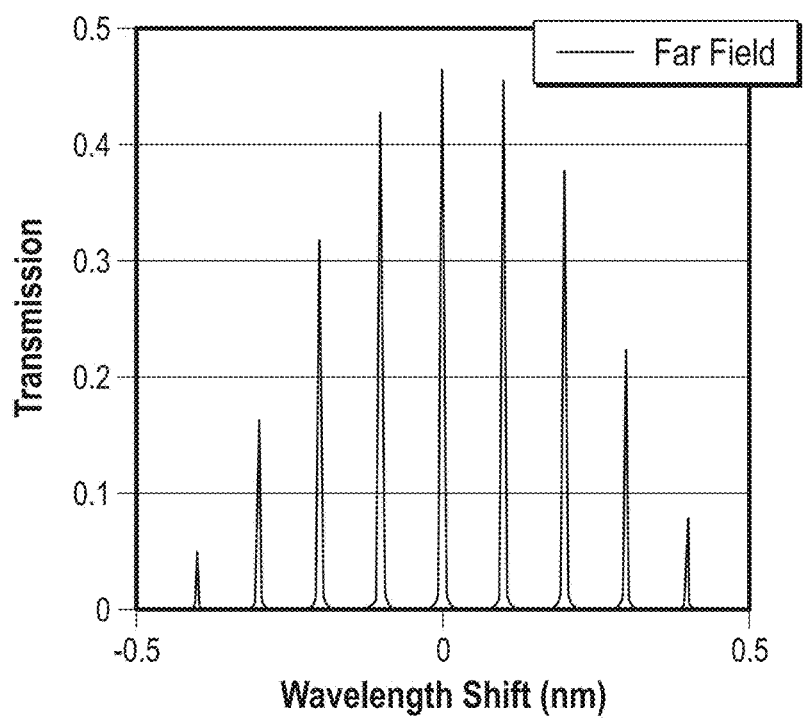
FIG. 2C depicts a combined passband far-field channel plot for a post-far-field filter return signal, in accordance with an embodiment.

The far-field channel includes far-field filter 408. In embodiments, far-field filter 408 may be an interference filter having a double cavity design, similar to filter 404. Far-field filter 405 may have the passband depicted by passband plot 604 of FIG. 2A. Passband plot 604 represents a fit to a measured filter transmission for a full width half maximum passband of 750 pm that remains relatively constant between 828.2 and 828.4 nm. In an embodiment, filter 408 may have a double cavity design, providing a substantially flat passband, as may be seen in passband plot 604. Advantageously, this may maximize the first and second laser wavelength throughput while minimizing the angle tuning effects for the filter transmission at lower ranges that can affect the accuracy of the number density retrieval of the target molecular species. FIG. 2C depicts the combined passband for the return signal in far-field channel received after filter 408.

The far-field channel next includes reducing lenses 410. In embodiments, reducing lenses 410 may reduce the diameter of the return signal beam approximately four times. For example, reducing lenses 410 may include a beam reducing pair of optics sized 80 mm and 19 mm to not exceed the numerical aperture of fiber 413. The return signal beam in the far-field channel is next focused via far-field focusing lens 411 onto fiber 413. In an embodiment, far-field focusing lens 411 may be an 11 mm focal length lens. In an embodiment, fiber 413 may be a multimode optical fiber with a 105 µm core diameter and a numerical aperture of 0.22, acting as a field stop to produce a narrow FOV of 115 µrad corresponding to the far-field.

Fiber 413 may then transmit the far-field channel of the return signal to fiber-coupled far-field photon counter 412. In embodiments, fiber-coupled far-field photon counter 412 may be a silicon avalanche photon detector operated in the Geiger mode.

Figure 4:
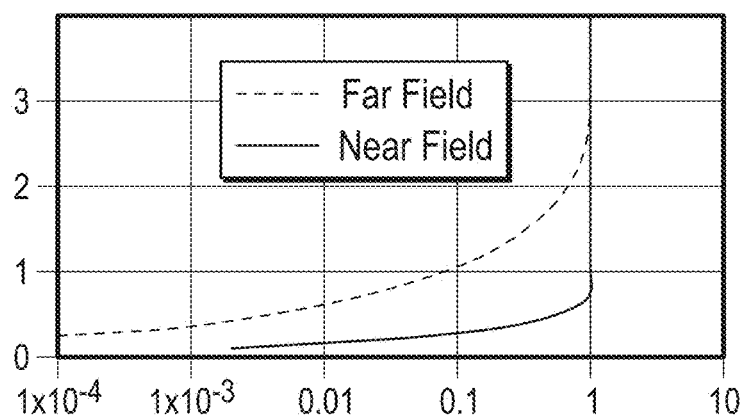
FIG. 4 depicts the overlap between a return signal at a photon counter, in accordance with an embodiment.

For each of the photon counters 412 and 416, full overlap occurs when the image of the return signal beam diameter is less than the diameter of the field stop. FIG. 4 depicts the overlap between the return signal at photon counters 412 and 416 in an example embodiment. FIG. 4 includes far-field overlap 606 and near-field overlap 607, wherein the x-axis represents the optical collection efficiency and the y-axis represents altitude in kilometers. It may be seen that far-field overlap 606 achieves full overlap at ranges greater than 2.75 km, whereas the near-field overlap 607 achieves full overlap at approximately 700 meters. Because the return signal has a dependence of $r^{-2}$, the near-field channel will detect a greater signal at lower ranges. However, the near-field return signal will also have substantially higher amount of noise during daytime because it collects 16 times more background light compared to the far-field channel because the background light collected is proportional to the square of the field of view. Therefore, only the lowest range gates of the near-field channel are useful during daytime. For these reasons, the near-field channel is most useful when operating micropulse differential absorption LIDAR 100 at short temporal and spatial resolutions, such as 1 min and 75 m, respectively.

Advantageously, the multi-stage optical filtering provided by etalon 402 and filters 404 and 408 suppress the background while minimally affecting the return signal allowing for the discrimination of return signal photons against a bright background. This is especially helpful when taking measurements of molecular species during the daytime and in cloudy conditions when the high background signal can easily saturate a photon counter and is often larger than the desired signal.

Electronics

Micropulse differential absorption LIDAR 100 further includes electronics 500. Electronics 500 includes pulse generator 502, digital IO board 504, laser transmission enable switch 506, computer 508, second laser return signal switch 512, multi-channel photon counter 514, first laser return signal switch 516, wavelength meter 518, and diode controller 520.

Electronics 500 is operable to command, operate, and/or collect telemetry from any component of micropulse differential absorption LIDAR 100, including beam transmitter 200, shared optics and telescope 300, optical receiver 400, or any component integrated into electronics 500, as described below. In embodiments, electronics 500 may operate using transistor-to-transistor logic (TTL). In other embodiments, electronics 500 may operate according to any other digital logic known to those of skill in the art.

Electronics 500 includes pulse generator 502. In embodiments, pulse generator 502 may be utilized as a master clock for micropulse differential absorption LIDAR 100. For example, a leading edge from pulse generator 502 may be used to substantially concurrently pulse the laser signals provided by first laser 202 and second laser 204 in beam transmitter 200. Pulse generator 502 may further be used to distinguish between a first and second laser wavelength when counting photons in the return signal.

In embodiments, electronics 500 may include digital IO 504. Digital IO 504 includes at least one digital input, two digital outputs, and a connection to computer 508. Digital IO 504 may receive a leading edge of the signal generated by pulse generator 502 at a digital input, and operate a toggle timer by counting a predefined number of pulses from pulse generator 502. For example, if pulse generator 502 is operating at 9 kHz, toggle timer may count 150 leading edges from pulse generator 502 to operate at 60 Hz. The toggle timer included on digital IO may signal the changes in toggle timer using two digital output lines to indicate high and low states.

Electronics 500 further includes laser transmission enable switch 506. Laser transmission enable switch 506 may be used to include signals alternatively from first laser 202 and second laser 204 in the transmission beam by switching either first switch 210 or second switch 212 alternatively on. Laser transmission enable switch 506 may use the signal from the toggle timer to initiate toggling between switch 210 and switch 212.

Electronics 500 further includes first laser return switch 516. First laser return switch 516 is operable to receive the signal from the toggle timer, and to toggle between transmitting an output signal from photon counter 416 to a first counter if the return signal includes backscattered light from the first laser signal and to the second counter if the return signal includes backscattered light from the second laser signal.

Laser transmission beam selection switch 506 and first laser return signal switch 516 may be toggled substantially concurrently by the toggle timer. Advantageously, by synchronizing the inclusion of the signal from first laser 202 in the transmission beam with the inclusion of return signal including backscattered light from the first laser signal in a dedicated first counter, or the inclusion of the signal from second laser 204 in the transmission beam with the inclusion of return signal including backscattered light from the second laser signal in a dedicated second counter, it is possible to improve the duty cycle and general performance of micropulse differential absorption LIDAR 100.

Electronics 500 may further include second laser return switch 512. Similar to first laser return switch 516, second laser return switch 512 is operable to receive the signal from the toggle timer, and to toggle between transmitting an output signal from photon counter 416 to a third counter if the return signal includes backscattered light from the first laser signal and to the fourth counter if the return signal includes backscattered light from the second laser signal. In embodiments, the first laser signal may include an offline laser signal and the second laser signal may include an online laser signal. In further embodiments, first laser return switch 516 may receive a near-field portion of the return signal from photon counter 416, and second laser return switch 512 may receive a far-field portion of the return signal from photon counter 512.

In example embodiments, laser transmission beam selection switch 506, first laser return signal switch 516, and second laser return signal switch 512 may be radio frequency (RF) electronic switches. In embodiments, electronics 500 may include multi-channel scalar 514. Multi-channel scalar 514 may include first counter, second counter, third counter, and fourth counter. In an example embodiment, multi-channel scalar 514 may be a four channel 20-MHz and 16 bit Sigma Space Corporation multi-channel scalar. In an example embodiment, if 10,000 samples may be accumulated with a bin duration of 500 ns and 220 bins with a 1.1 second acquisition time. If the approximate 1-μs pulse duration (150-m in range) is over-sampled by multi-channel scalar 514, this may yield 2 data points per 150 m, corresponding to a sampled vertical range resolution of 75 m. The summing of these 75-m bins may be performed during post processing where 2 bins are grouped together to yield a 150-m range resolution for micropulse differential absorption LIDAR 100.

Laser transmission enable switch 506 may further be used to modulate the laser signals into pulses, resulting in a transmission beam that includes alternating groups of laser pulses from first laser 202 and second laser 204. Laser transmission enable switch 506 may receive both pulses from pulse generator 502 and signals from the toggle timer. Laser transmission enable switch 506 may provide one first laser 202 pulse in the transmission beam by switching first switch 210 on upon receiving of a pulse from pulse generator 502 and a first state signal from the toggle timer. Laser transmission enable switch 506 may provide one second laser 204 pulse in the transmission beam by switching second switch 212 on upon receiving of a pulse from pulse generator 502 and a second state signal from the toggle timer, wherein the first state signal is different from the second state signal.

Electronics 500 may further include laser transmission beam selection switch 214. Laser transmission beam selection switch 214 is a 2×1 switch operable to receive both laser pulses from first switch 210 and second switch 212, but to transmit only one of the pulses from first switch 210 and second switch 212 in the transmission beam. The toggle timer may be used to select which of the received laser pulses will be included in the transmission beam. Advantageously, using two-stage switching with first switch 210 and second switch 212 may provide for better isolation in the transmission beam, as discussed above.

Electronics 500 may further operate amplifier 222 via pulse generator 502 so that amplifier 222 is substantially concurrently switched on at the same time that laser transmission enable switch 506 allows laser signal to pass. If amplifier 222 is a TSOA, a large number of scattered photons in the outgoing pulse in the transmission beam may prohibit measuring the atmospheric return during the initial period following when laser transmission enable switch 506 toggles between including signal from the first laser 202 and the second laser 204 in the transmission beam. Therefore, in the example operational configuration described above with 1.1 μs laser pulse width in the transmission beam, the lowest usable range gate for micropulse differential absorption LIDAR 100 is 225 m. Electronics 500 may be used in a number of configurations, however. In a further example, if electronics 500 is programmed to include 500 ns duration laser pulses in the transmission beam, the lowest usable gate may be reduced to a 75 m range. Albeit, the amplified laser pulse would be 300 ns in duration with roughly ⅓ of the energy per pulse.

Advantageously, electronics 500 may provide improved isolation of signal in the transmission beam, minimize the buffer crosstalk problems experienced by previous micropulse differential absorption LIDAR systems, and increase duty cycle.

Prototype Testing

A prototype micropulse differential absorption LIDAR 100, a water vapor differential aborption LIDAR (WV-DIAL) was built and autonomously operated in Erie, Colo., USA during the Front Range Air Pollution and Photochemistry Experiment (FRAPPE) between 1 Jul. 2014 and 19 Aug. 2014. The prototype WV-DIAL operated near continuously for 50 days with an uptime of >95%. The shared optics and telescope 300 design proved to be stable, requiring no re-alignments. No measurable degradation in performance was detected in the prototype micropulse differential absorption LIDAR 100 during the field campaign.

The continuous observations of relative backscatter return signal illustrated the diurnal variation in the top of the aerosol layer and clearly identified cloud occurrences up to 12 km above ground level. The water vapor profiles produced using the prototype WV-DIAL provided data up to cloud base, illustrating substantial temporal variability and strong vertical gradients in the atmosphere above the instrument. Count rates for the far-range channel remained within the linear count regime for the photon counter, or below 1 Mc/s for all conditions encountered during the project. The maximum count rate for the near-range channel exceeded the linear count rate during the daytime and in bright cloudy conditions, however. These periods had to be filtered out of the data when retrieving the water vapor profiles.

During FRAPPE, there were 2 nighttime soundings and 43 daytime soundings. The large number of daytime sondes allowed for comparisons with the DIAL during periods of high background solar radiation, the most difficult data collection conditions for the prototype DIAL instrument. The mean water vapor error was found to be less than 10% for all of the radiosonde comparisons, from 300 m to 4 km above ground level.

The prototype WV-DIAL was collocated with a continually-operating passive infrared radiometer, an Atmospheric Emitted Radiance Interferometer (AERI). AERI utilizes an interference technique to retrieve atmospheric emitted radiance. Starting with initial temperature and humidity profiles based on statistical models, an iterative solution to the radiative transfer equations is utilized to reproduce the measured atmospheric emitted radiance. This iterative solution provides the final temperature and WV profiles for clear sky conditions up to approximately 3 km. During cloudy conditions, retrievals are sensitive to the cloud properties leading to larger errors in the temperature and WV profiles, so a separate measurement of the cloud base height is often required.

Figure 5:
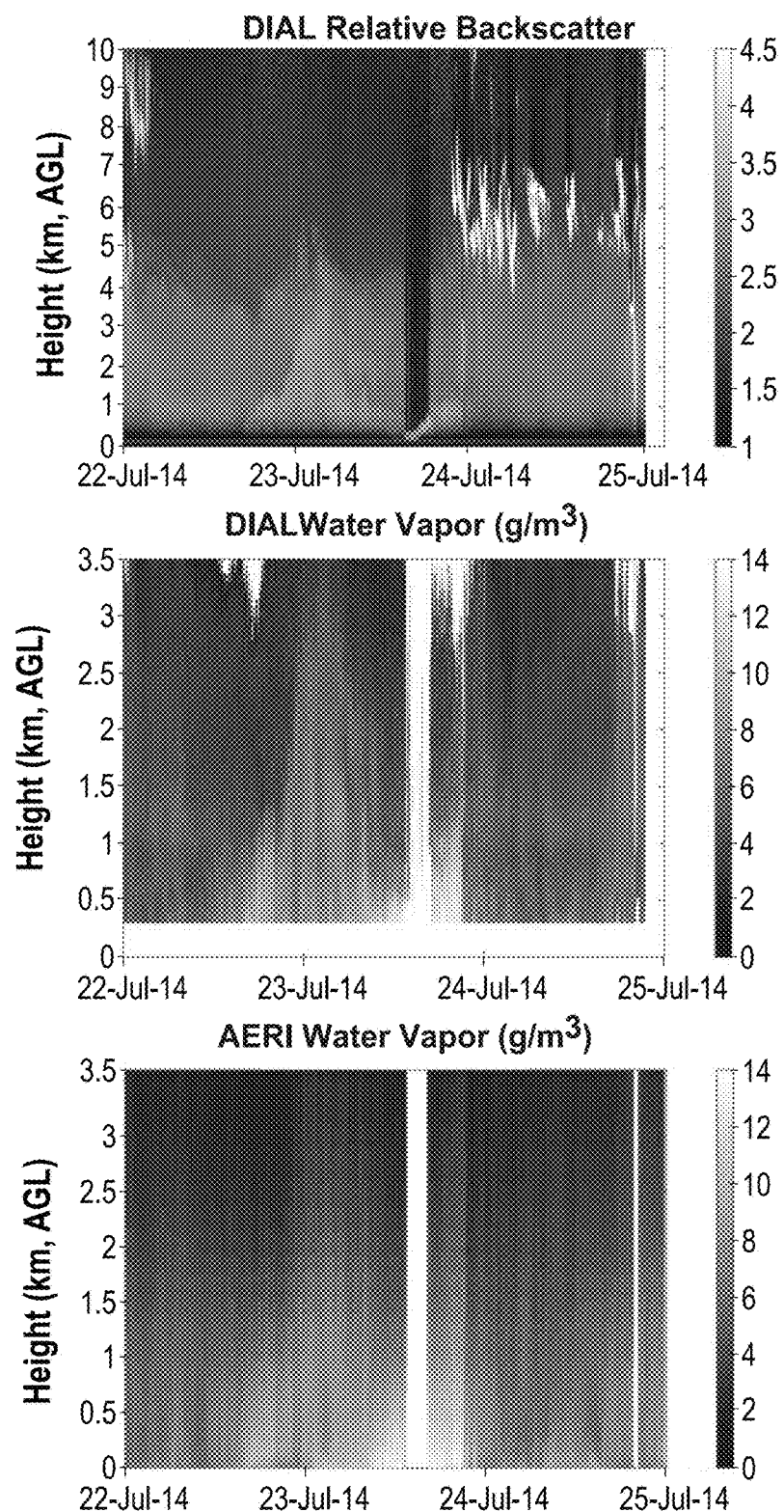
FIG. 5 depicts data from a prototype micropulse differential absorption LIDAR and an AERI instrument, in accordance with an embodiment.

A preliminary comparison between the AERI with the WV DIAL data is included FIG. 5. FIG. 5 for a set of data taken between 22-25 Jul. 2014. Plot 702 depicts the relative backscatter detected with the prototype WV-DIAL, and plot 704 depicts the water vapor determined from the WV-DIAL data. Plot 706 depicts the AERI retrievals, which include continuous profiles of water vapor up to 3.5 km. The AERI profiles were retrieved every 10 min with a vertical resolution of 30 m at the surface decreasing to 600 m at 3 km. The WV-DIAL data were processed with 1 min averaging and a vertical resolution of 150 m (300 m smoothing were applied to the data above 3 km).

A comparable buildup in moisture may be seen leading into 23 July between plots 704 and 706, the increasing moisture values and depth are similarly observed by both instruments. The AERI and WV-DIAL are both limited in times of fog, as may be seen in plots 704 and 706 before 24 July. Both datasets show a similarly dramatic decrease in moisture just prior to 24 July, which may have been caused by a frontal passage or other change in wind direction. Prior to this abrupt change, there appears to be an absolute humidity inversion in the DIAL data of plot 704, which cannot be observed with a passive remote sensor such as AERI. A comparable buildup in moisture quantity and depth may then be seen in plots 704 and 706 at the end of the time series leading into 25 July.

Data from the FRAPPE campaign and the related sounding data demonstrated the capability of the prototype WV-DIAL to provide accurate measurements of water vapor in continual operation for an extended period of time in a variety of atmospheric conditions.

The detailed descriptions of the above embodiments are not exhaustive descriptions of all embodiments contemplated by the inventors to be within the scope of the Application. Indeed, persons skilled in the art will recognize that certain elements of the above-described embodiments may variously be combined or eliminated to create further embodiments, and such further embodiments fall within the scope and teachings of the Application. It will also be apparent to those of ordinary skill in the art that the above-described embodiments may be combined in whole or in part to create additional embodiments within the scope and teachings of the Application.

We claim:

1. A micropulse differential absorption LIDAR comprising:
a first laser signal;
a second laser signal having a different wavelength than the first laser signal;

a laser transmission beam selection switch operable to toggle, upon receiving a timing pulse from a toggle timer, between including only one of the first laser signal or the second laser signal in a transmission beam;

a first laser return signal switch operable to toggle between a first counter when the return signal includes a backscattered light from the first laser signal and a second counter when the return signal includes a backscattered light from the second laser signal; and the toggle timer operable to substantially concurrently toggle the laser transmission beam selection switch and the first laser return signal switch.

2. The micropulse differential absorption LIDAR of claim 1, further comprising:
a pulse generator;
wherein the toggle timer counts a predetermined number of pulses from the pulse generator before concurrently toggling the laser transmission beam selection switch and the first laser return signal switch.

3. The micropulse differential absorption LIDAR of claim 2, further comprising:
a laser transmission enable switch;
a first laser switch operable to modulate the first laser return signal in the transmission beam when triggered by the laser transmission enable switch;
a second laser switch operable to modulate the second laser return signal in the transmission beam when triggered by the laser transmission enable switch;
wherein the laser transmission enable switch is triggered by the pulse generator, the laser transmission enable switch alternates between the first laser switch and the second laser switch when toggled by the toggle timer.

4. The micropulse differential absorption LIDAR of claim 3, further comprising:
an amplifier operable to amplify the transmission beam;
wherein the amplifier is toggled on and off by the pulse generator.

5. The micropulse differential absorption LIDAR of claim 3, wherein the laser transmission beam selection switch and the laser return signal switch are radio frequency switches.

6. The micropulse differential absorption LIDAR of claim 3, further comprising:
a second laser return signal switch operable to toggle between a third counter when the return signal includes the backscattered light from the first laser signal, and a fourth counter when the return signal includes the backscattered light from the second laser signal; wherein the toggle timer toggles the second laser transmission beam selection switch.

7. The micropulse differential absorption LIDAR of claim 3, wherein the return signal includes a near-field return signal and a far-field return signal, and the first counter and the second counter are operable to determine the strength of the near-field return signal and the third counter and the fourth counter are operable to determine the strength of the far-field return signal.

8. The micropulse differential absorption LIDAR of claim 3, wherein the first laser signal includes an online frequency and the second laser signal includes an offline frequency.

9. The micropulse differential absorption LIDAR of claim 6, wherein the first counter, the second counter, the third counter, and the fourth counter are included in a multi channel scalar.

10. The micropulse differential absorption LIDAR of claim 2, further comprising:
a computer;
wherein the pulse generator initiates sending a first counter value and a second counter value to the computer.

11. A method for operating a micropulse differential absorption LIDAR, the method comprising the steps of:
receiving a first laser signal;
receiving a second laser signal having a different wavelength than the first laser signal;
upon receiving a timing pulse from a toggle timer, toggling between including only one of the first laser signal and the second laser signal in a transmission beam using a laser transmission beam selection switch;
toggling between a first counter when the return signal includes a backscattered light from the first laser signal and a second counter when the return signal includes a backscattered light from the second laser signal using a first laser return signal switch; and
toggling the laser transmission beam selection switch and the first laser return signal switch substantially concurrently using the toggle timer.

12. The method claim 11, further comprising the steps of:
counting a predetermined number of pulses received from a pulse generator using the toggle timer before concurrently toggling the laser transmission beam selection switch and the first laser return signal switch.

13. The method of claim 12, further comprising the step of:
amplifying the transmission beam, the amplifier toggled on and off by the pulse generator.

14. The method of claim 12, wherein the laser transmission beam selection switch and the laser return signal switch are radio frequency switches.

15. The method of claim 11, further comprising the steps of:
toggling between a third counter when the return signal includes the backscattered light from the first laser signal and a fourth counter when the return signal includes the backscattered light from the second laser signal using a second laser return signal switch, wherein the toggle timer toggles the second laser transmission beam selection switch.

16. The method of claim 11, wherein the return signal includes a near-field return signal and a far-field return signal, and the first counter and the second counter are operable to determine the strength of the near-field return signal and the third counter and the fourth counter are operable to determine the strength of the far-field return signal.

17. The method of claim 11, wherein the first laser signal includes an online frequency and the second laser signal includes an offline frequency.

18. The method of claim 15, wherein the first counter, the second counter, the third counter, and the fourth counter included in a multi channel scalar.

* * * * *